United States Patent
Ui et al.

(10) Patent No.: US 9,910,023 B2
(45) Date of Patent: Mar. 6, 2018

(54) GAS SENSOR

(71) Applicants: FUJI ELECTRIC CO., LTD., Kawasaki-shi (JP); The University of Tokyo, Tokyo (JP)

(72) Inventors: Fumi Ui, Kawasaki (JP); Takuya Suzuki, Kawasaki (JP); Jean-Jacques Delaunay, Tokyo (JP)

(73) Assignees: FUJI ELECTRIC CO., LTD., Kawasaki-Shi (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/198,458

(22) Filed: Jun. 30, 2016

(65) Prior Publication Data

US 2017/0010246 A1  Jan. 12, 2017

(30) Foreign Application Priority Data

Jul. 10, 2015 (JP) ................................. 2015-138394

(51) Int. Cl.
  *G01N 27/00* (2006.01)
  *G01N 33/00* (2006.01)
  *G01N 27/12* (2006.01)

(52) U.S. Cl.
  CPC ....... *G01N 33/0047* (2013.01); *G01N 27/123* (2013.01); *G01N 33/0016* (2013.01); *G01N 33/0073* (2013.01)

(58) Field of Classification Search
  CPC .......... G01N 27/4074; G01N 27/4141; G01N 27/4072
  USPC .............................. 422/82.92, 88, 83, 82.02
  See application file for complete search history.

(56) References Cited

U.S. PATENT DOCUMENTS

2003/0159928 A1* 8/2003 Kojima .............. G01N 27/4067
                                                           204/408

FOREIGN PATENT DOCUMENTS

| JP | 2002-286674 A | 10/2002 |
| JP | 2005-017242 A | 1/2005 |
| JP | 2005-164566 A | 6/2005 |
| JP | 2005-315874 A | 11/2005 |

* cited by examiner

*Primary Examiner* — Natalia Levkovich
(74) *Attorney, Agent, or Firm* — Rabin & Berdo, P.C.

(57) ABSTRACT

A gas sensor having a heater layer; and a gas detector that is heated by the heater layer to detect a measurement target gas. The gas detector has a gas sensing layer, a diffusion layer that covers a surface of the gas sensing layer, and an absorption layer that covers a surface of the diffusion layer. The absorption layer has greater absorption of the measurement target gas than the diffusion layer, and the diffusion layer has greater diffusion of the measurement target gas than the absorption layer.

18 Claims, 8 Drawing Sheets

GAS SENSOR

CROSS REFERENCE TO RELATED APPLICATION

This non-provisional application for a U.S. patent is based upon and claims the benefit of priority from the prior Japanese Patent Application No. 2015-138394, filed on Aug. 7, 2015, the entire contents of which are incorporated herein by reference.

BACKGROUND OF THE INVENTION

1. Field of the Invention

The present invention relates to a gas sensor capable of detecting trace gas

2. Description of the Related Art

There are developed gas sensors for purposes of detecting gas leakage of methane gas ($CH_4$), propane gas ($C_3H_8$), carbon monoxide (CO) and the like, and imperfect combustion, as well as for detecting and analyzing volatile organic compounds (VOC).

When a gas sensor is used as a gas leak detector for methane gas or the like, the gas sensor has only to detect the gas in the order of 1000 to 10000 ppm below the explosion limit, and in the case of imperfect combustion, a gas sensor has only to detect the gas in the order of 10 to 100 ppm in order to prevent carbon monoxide poisoning to people.

On the other hand, when a gas sensor is used as a gas sensor for room environment analysis or a breath sensor for health management, the gas sensor needs to detect trace measurement target gas such as volatile organic compounds in the order of 0.001 to 10 ppm highly sensitively.

Japanese Patent Application Publication No. 2005-17242 (hereinafter referred to as "JP2005-017242") and Japanese Patent Application Publication No. 2005-164566 (hereinafter referred to as "JP2005-164566") disclose a gas leak detector for methane gas and a gas sensor for imperfect combustion. On the other hand, Japanese Patent Application Publication No. 2005-315874 (hereinafter referred to as "JP2005-315874") discloses a gas sensor that is able to detect volatile organic compounds, combustible gas and poisonous gas.

According the invention of JP 2005-315874, a coating layer having ceramic particles of 8 to 30 nm is provided on an electrode and the coating layer is formed, for example of $SnO_2$. According to JP2005-315874, the coating layer itself serves as a gas sensing layer that reacts with a measurement target gas and the measurement target gas is detected by change in resistance value of the coating layer. Thus, according to JP2005-315874, the gas detector has been improved in structure, but no improvement has been made to the layer structure for coating the surface of the gas sensing layer to increase the detection sensitivity.

In the structure where the gas sensing layer has been improved to improve the detection sensitivity as disclosed in JP2005-315874, there appears to be difficulty in improving the detection sensitivity for various kings of trace gases, depending on various purposes, simply and appropriately.

Conventionally there is no gas sensor that is capable of detecting trace measurement target gas such as volatile organic compounds highly sensitively.

SUMMARY OF THE INVENTION

The present invention was carried out in view of the foregoing and aims to provide a gas sensor capable of detecting trace gas to measure with high sensitivity.

One aspect of the present invention is a gas sensor comprising: a heater layer; and a gas detector that is heated by the heater layer to detect a measurement target gas, wherein the gas detector has a gas sensing layer, a diffusion layer that covers a surface of the gas sensing layer, and an absorption layer that covers a surface of the diffusion layer, the absorption layer has a more excellent absorption property of the measurement target gas than the diffusion layer, and the diffusion layer has a more excellent diffusion property of the measurement target gas than the absorption layer.

Another aspect of the present invention is characterized in that in the above-mentioned gas sensor, the absorption layer is formed of a first porous layer having an excellent absorption property, the diffusion layer is formed of a second porous layer having an excellent diffusion property, and an average pore size of the first porous layer is smaller than an average pore size of the second porous layer.

Yet another aspect of the present invention is characterized in that in the above-mentioned gas sensor, the second porous layer comprises two or more layers, and a layer of the second porous layer closer to the gas sensing layer has a greater average pore size.

Still yet another aspect of the present invention is characterized in that the above-mentioned gas sensor further comprises a controller that controls to drive the heater layer and obtains a sensor output from the gas sensing layer, the controller controls to drive the heater layer intermittently, and the measurement target gas supplied from the diffusion layer is detected when there occurs a reaction between the measurement target gas and the gas sensing layer. Then, according to the present invention, the measurement target gas is absorbed to the absorption layer while driving of the heater layer is stopped, and the measurement target gas is thermally desorbed from the absorption layer by driving the heater layer and is diffused in the diffusion layer toward the gas sensing layer.

Still yet another aspect of the present invention is characterized in that in the above-mentioned gas sensor, the first porous layer and the second porous layer are different in at least one of average particle size, specific surface area, polarity, film thickness, supported metal and material.

Still yet another aspect of the present invention is characterized in that in the above-mentioned gas sensor, the absorption layer and the diffusion layer are each composed of at least one metal oxide selected from $Al_2O_3$, $Cr_2O_3$, $Fe_2O_3$, $Ni_2O_3$, $ZrO_2$ and $SiO_2$ as a main ingredient.

Still yet another aspect of the present invention is characterized in that in the above-mentioned gas sensor, an oxygen supply layer is formed at least on the surface of the gas sensing layer.

Still yet another aspect of the present invention is characterized in that in the above-mentioned gas sensor, the gas sensing layer is formed of a metal oxide layer containing dopant.

Still yet another aspect of the present invention is characterized in that the above-mentioned gas sensor comprises: a substrate; a heat insulating layer formed on a surface of the substrate; the heater layer formed on a surface of the heat insulating layer; an electric insulating layer formed on a surface of the heater layer; the gas sensing layer formed on a surface of the electric insulating layer; an electrode layer connected to the gas sensing layer; the diffusion layer formed on the surface of the gas sensing layer; and the absorption layer formed on the surface of the diffusion layer, and the substrate has a through hole formed communicating with the heat insulating layer or has a closed-end cavity formed between the substrate and the heat insulating layer.

DETAILED DESCRIPTION OF THE INVENTION

An embodiment of the present invention will be described in detail below. Note the present invention is not limited to the following embodiments and may be modified variously without departing from the scope of the invention.

Figure 1:
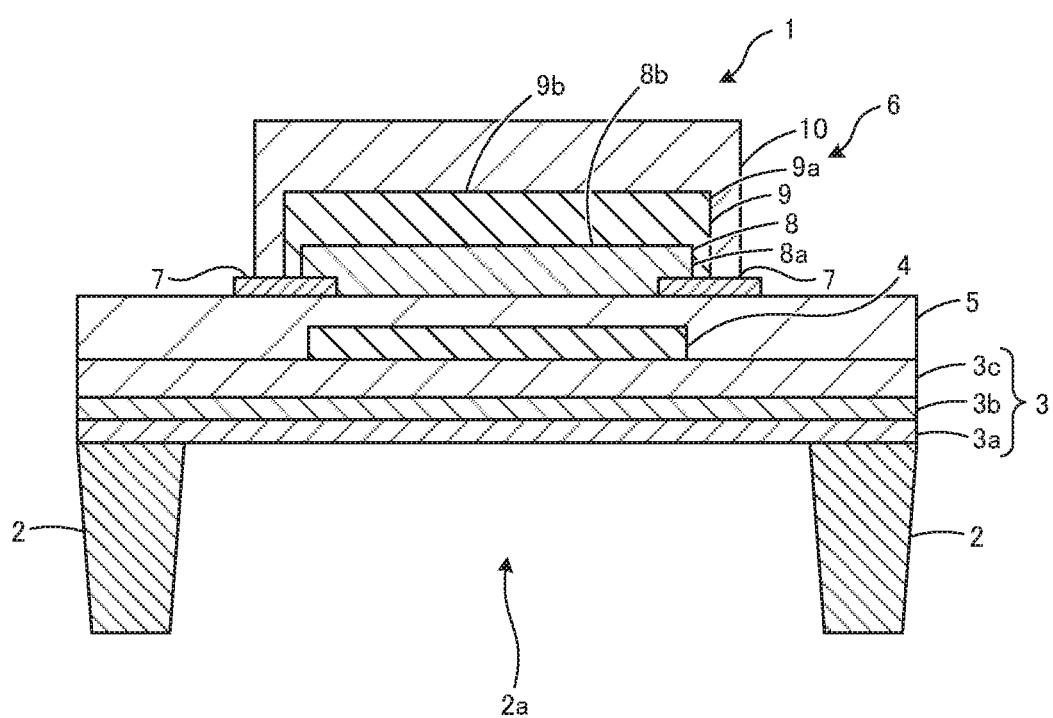
FIG. 1 is a longitudinal sectional view of a gas sensor according to a first embodiment.

FIG. 1 is a longitudinal sectional view of a gas sensor according to the first embodiment. The gas sensor 1 is a semiconductor-type gas sensor and is configured to detect a gas on the basis of a resistance value that changes depending on reaction caused between the gas sensor and a gas sticking to the gas sensing layer.

The gas sensor 1 illustrated in FIG. 1 is configured to have a silicon substrate 2, a heat insulating layer 3, a heater layer 4, an electric insulating layer 5 and a gas detector 6 for detecting a measurement target gas. Here, the gas sensor 1 in FIG. 1 is schematically presented for illustrative purposes only and the shape of each layer and the film thickness ratio as shown in FIG. 1 are allowed to be different from those of actual products. The same goes for FIG. 2 and later.

As illustrated in FIG. 1, the silicon substrate 2 has a through hole 2a formed therein that passes from the upper surface of the substrate and the bottom surface of the substrate. As illustrated in FIG. 1, the heat insulating layer 3 is formed to over an upper opening part of the through hole 2a at the surface of the silicon substrate 2. The heat insulating layer 3 has the form of a diaphragm (hereinafter referred to as "diaphragm structure").

The heat insulating layer 3 illustrated in FIG. 1 has, as one example, a thermal oxidation $SiO_2$ layer 3a, a CVD-$Si_3N_4$ layer 3b and a CVD-$SiO_2$ layer 3c that are stacked in this order. Out of these layers, the thermal oxidation $SiO_2$ layer 3a has the function of reducing the heat capacity by preventing conduction of heat generated in the heater layer 4 to the silicon substrate 2 side, and the thermal oxidation $SiO_2$ layer 3a has strong resistance to plasma etching so that the through hole 2a can be formed appropriately in the silicon substrate 2 by plasma etching. In addition, the CVD-$SiO_2$ layer 3c is a layer configured to enhance the adhesion to the heater layer 4 and also to ensure excellent electric insulation. The materials and layer structure of the heat insulating layer 3 may be modified appropriately.

Figure 4:
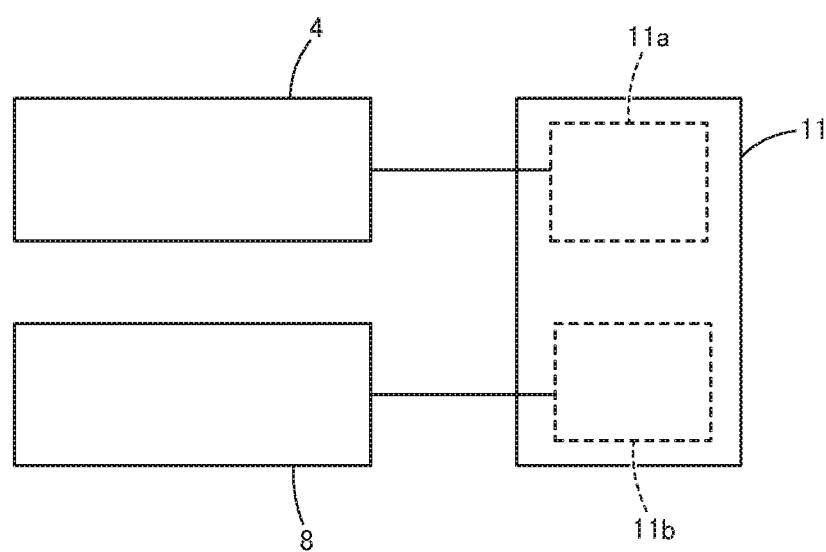
FIG. 4 is a block diagram of a gas sensor.

As illustrated in FIG. 1, the heater layer 4 is formed on the surface of the heat insulating layer 3. The material of the heater layer 4 is not limited specifically, but is, for example, formed of a thin film shape Pt—W film. In addition, the shape of the heater layer 4 is not limited specifically, but is formed, for example, into a meandering shape. Further, as not illustrated, the heater layer 4 is connected to a heater controller 11a that constitutes a controller 11 as illustrated in FIG. 4 via a wiring layer.

As illustrated in FIG. 1, the electric insulating layer 5 is formed to cover the surface of the heater layer 4 and the surface of the heat insulating layer 3. The electric insulating layer 5 is, for example, a $SiO_2$ sputter layer. The electric insulating layer 5 is a layer for ensuring electric insulation between the heater layer 4 and sensing layer electrodes 7. Further, the electric insulating layer 5 is excellent in adhesion to the gas sensing layer 8.

As illustrated in FIG. 1, the gas detector 6 is configured to have the sensing layer electrodes 7, the gas sensing layer 8, a diffusion layer 9 and an absorption layer 10. The sensing layer electrodes 7 are formed on the surface of the electric insulating layer 5. For example, the sensing layer electrodes 7 are formed of Pt or Au, but are not limited these. As illustrated in FIG. 1, the sensing layer electrodes 7 are provided in pair as shown at the right and left sides of the figure.

As illustrated in FIG. 1, the gas sensing layer 8 is provided partially overlapping the sensing layer electrodes 7 and laying over the surface of the electric insulating layer 5. As illustrated in FIG. 4, the gas sensing layer 8 is connected to a calculator 11b that forms the controller 11. The gas sensing layer 8 is formed of a metal oxidation layer and specifically, it is preferably a $SnO_2$ layer. The material of the gas sensing layer 8 is not limited to $SnO_2$, but the gas sensing layer 8 may be formed of a thin film layer having $In_2O_3$, $WO_3$, ZnO, $TiO_2$ or the like as a main ingredient. In FIG. 1, the gas sensing layer 8 has an approximately rectangular shape, but the gas sensing layer 8 may be formed of a plurality of columns depending on sputtering conditions or the like thereby to be able to increase the surface area of the gas sensing layer 8. As the surface area of the gas sensing layer 8 is increased, it is possible to increase the reaction sensitivity with measurement target gas.

As illustrated in FIG. 1, the diffusion layer 9 is provided covering the surfaces of the gas sensing layer 8. As illustrated in FIG. 1, the diffusion layer 9 is formed covering the side surfaces 8a and the upper surface 8b of the gas sensing layer 8 and covering the surfaces of the gas sensing layer 8 entirely.

As illustrated in FIG. 1, the absorption layer 10 coves the surfaces of the diffusion layer 9. As illustrated in FIG. 1, the absorption layer 10 is formed covering the side surfaces 9a and the upper surface 9b of the diffusion layer 9 and covering the surfaces of the diffusion layer 9 entirely. In the structure illustrated in FIG. 1, the absorption layer 10 forms the uppermost surface of the gas sensor.

As described above, the diffusion layer 9 covers the surfaces of the gas sensing layer 8 entirely and the absorption layer 10 covers the surfaces of the diffusion layer 9 entirely. With this structure, it is possible to detect a gas appropriately even if the gas is detected not only in the upper direction, but also in the lateral direction with respect to the gas sensor.

Otherwise, a layer (not shown) may be provided on the surface of the absorption layer 10, but in order to maintain the absorption function of the absorption layer 10 under the coating layer, the coating layer needs to be a gas-permeable layer that does not lose the absorption function of the absorption layer 10. Or, the coating layer may be a gas-impermeable layer and be provided covering only side parts of the abruption layer 10 to have directivity in the gas detecting direction.

The absorption layer 10 has more excellent absorption to measurement target gas than the diffusion layer 9 and the diffusion layer 9 has more excellent diffusion to the measurement target gas than the absorption layer 10. This point is described in detail below.

Figure 7:
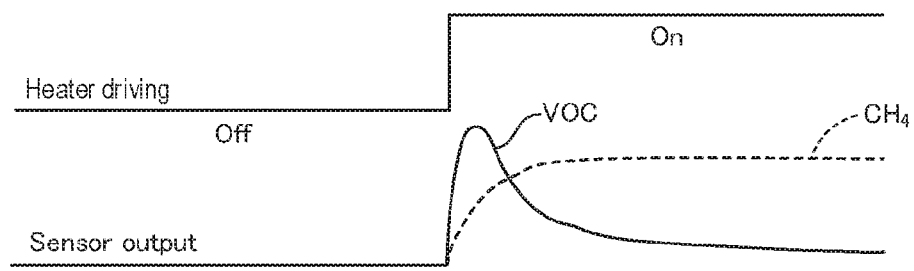
FIG. 7 is a chart showing the relationship between heater drive and sensor output.

For example, JP2005-017242 and JP2005-164566 disclose the invention of covering the surface of a gas sensing layer by a selective combustion layer and if the gas sensor is a methane gas sensor, gas other than methane gas is combustion-removed by the selective combustion layer and the methane gas is detected by the gas sensing layer. In this case, as illustrated in the chart of FIG. 7, when heater drive is on to heat the gas detector, a sensor output with respect to methane gas ($CH_4$) is obtained. Then, in the methane gas sensor, in order for not-measurement target gas other the methane gas to be combustion-removed, the selective combustion layer needs to be exposed to high temperatures (specifically, 400° C. or more) by driving of the heater layer. For example, the detection temperature of ammonia is approximately 150° C., the detection temperature of ethanol is approximately 230° C., and the detection temperature of acetone is approximately 260° C. By exposing the selective combustion layer to the high temperatures of 400° C. or more, it is possible to detect methane gas accurately. In addition, when the gas sensor is used as a gas leak detector for methane gas or the like, the gas sensor has only to detect the gas in the order of 1000 to 10000 ppm below the explosion limit, and in the case of imperfect combustion, the gas sensor has only to detect the gas in the order of 10 to 100 ppm in order to prevent carbon monoxide poisoning to people.

On the other hand, in the embodiment illustrated in FIG. 1, for example, the gas sensor is used as a gas sensor for room environment analysis or a breath sensor for health management, and the measurement target gas is trace volatile organic compounds in the order of 0.001 to 10 ppm or the like. In this embodiment, selective combustion is not performed as disclosed in JP2005-017242 and JP2005-164566, but the measurement target gas is absorbed to the gas sensor and diffusion is expedited inside the sensor thereby to detect trace gas highly sensitively. Therefore, in the present embodiment, the absorption layer 10 is provided as the uppermost layer of the gas sensor 1 and the diffusion layer 9 is provided between the gas sensing layer 8 and the absorption layer 10.

Figure 5A:
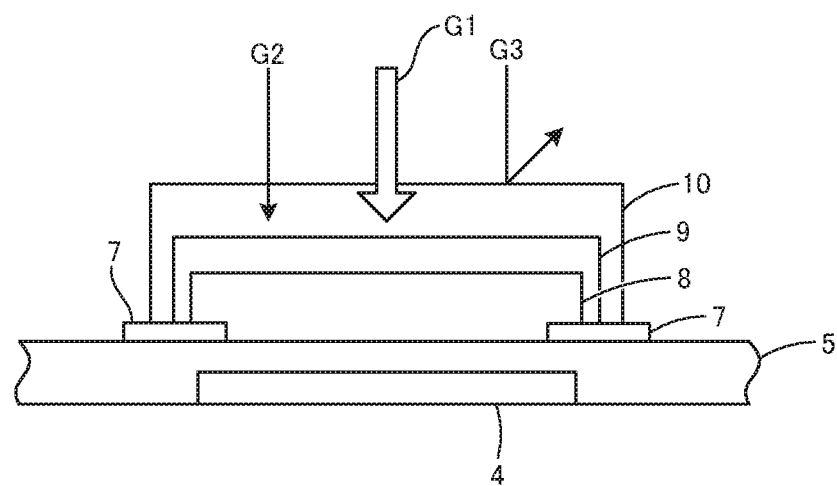
FIGS. 5A and 5B provide partial diagrams of the gas sensor for explaining the principle of detecting trace gas.
Figure 5B:
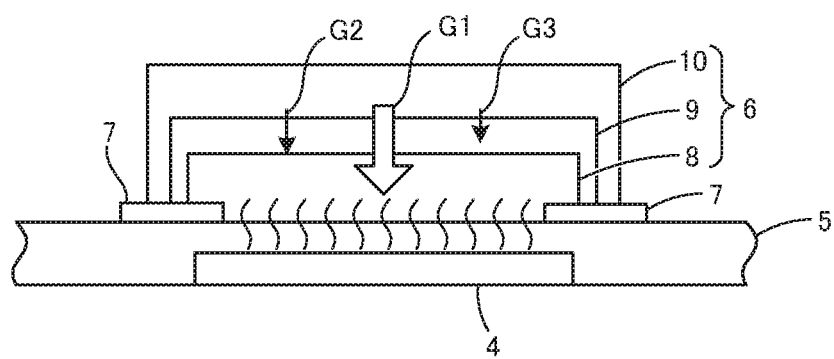

Next description is made about the detection principle of the gas sensor in the present embodiment. FIG. 5A is a diagram for explaining the absorption function mainly and FIG. 5B is a diagram for explaining the diffusion function mainly. In FIGS. 5A and 5B, the same reference numerals as those in FIG. 1 denote the same layers in FIG. 1.

In FIG. 5A (absorption step), the measurement target gas G1 is absorbed to the absorption layer 10 and condensed. For example, the absorption layer 10 is formed of a first porous layer having excellent absorption. Absorption and condensing of the measurement target gas G1 to the absorption layer 10 is mainly performed while driving of the heater layer 4 is stopped (while the heater drive is off in FIG. 7). Thus, in the present embodiment, first the measurement target gas G1 is absorbed and condensed to be held at the absorption layer 10.

Then, in FIG. 5B (diffusion step), the measurement target gas G1 absorbed to the absorption layer 10 is diffused in the diffusion layer 9 and is made to react with oxygen on the surface of the gas sensing layer 8 thereby to detect the gas by the gas sensing layer 8. Here, the arrows shown in FIGS. 5A and 5B denote gas absorption directions and gas diffusion directions. These are presented for easy explanation of the directions and gas directions are not limited to these. For example, in the diffusion direction in FIG. 5B, there is a gas that is discharged from the absorption layer 10 to the outside, but its discharge direction is not illustrated.

The diffusion step illustrated in FIG. 5B is performed in the state where the heater layer 4 is driven and the gas detector 6 is heated. By heating, the measurement target gas G1 absorbed and condensed to the absorption layer 10 is subjected to thermal desorption in a short time. The heating temperature at this stage is, for example, 300° C. or less. The measurement target gas G1 subjected to thermal desorption is, then, diffused in an expedited manner and absorbed to the surface of the gas sensing layer 8. In this embodiment, the measurement target gas G1 absorbed and condensed at the absorption layer is thermal desorption in an extremely short time (specifically, in 700 msec or less) and diffused from the diffusion layer 9 to the gas sensing layer 8. With this process, the measurement target gas G1 is able to be absorbed to the surface of the gas sensing layer 8 in high concentrations. Then, there occurs reaction between the oxygen on the surface of the gas sensing layer 8 and the measurement target gas G1, which causes change in resistance of the gas sensing layer 8, and this detection value is used as a basis to obtain a sensor output at the calculator 11b in FIG. 4. FIG. 7 shows the sensor output of volatile organic compounds (VOC) that is detected by the gas sensor according to the present embodiment is shown. As illustrated in FIG. 7, when the heater drive is changed from off to on, it is possible to obtain a sensor output in an extremely short time. In the calculator 11b in FIG. 4, it is possible to detect the concentration of the measurement target gas G1 based on the sensor output.

For example, the diffusion layer 9 is formed of a second porous layer that is excellent in diffusion. The above-mentioned first porous layer and the second porous layer are both layers on which a plurality of porous materials (porous particles) are deposited and a binder resin may be provided between the porous materials. For example, the second porous layer is formed to have a larger average pore size than the first porous layer. With this feature, the first porous layer is formed to have more excellent absorption with respect to the measurement target gas G1 than the second porous layer and the second porous layer is formed to have more excellent diffusion with respect to the measurement target gas G1 than the first porous layer. Other than the average pore size, the average particle size, specific surface area, polarity, film thickness, supported metal and material are also controlled thereby to control absorption and diffusion. In the present embodiment, one or two or more of the average pore size, average particle size, specific surface area, polarity, film thickness, supported metal and material may be differentiated between the first porous layer and the second porous layer. The average pore size is an average size of a large number of pores formed in the plurality of porous materials (porous particles) that constitute the porous layer, and for example, the average pore size can be obtained by the BJH method. The BJH method is a method for obtaining an average pore size from desorption isotherm that indicates the relationship between an absorption amount and a relative pressure when the adsorbate is desorbed. A measurement device used in the BJH method is, for example, a BEL-SORP-mini by Microtrac BEL Corp. Or, the average pore size may be obtained from an arithmetic average value of equivalent circle diameters of pores shown in the surface of a given number of (for example, 10) particles when it is measured using an observation tool such as a scanning electron microscope (SEM) or a transmission electron microscope (TEM). The average particle size is defined as an arithmetic average value of particle sizes of a given number of (for example, 10) particles when it is measured using an observation tool such as a scanning electron microscope (SEM) or a transmission electron microscope (TEM). The specific surface area represents the surface area per unit weight, and for example, means a specific surface area obtained by the BET method ($N_2$). In addition, the "polarity" is a property of carrying positive or negative electrical charge and can be adjusted by the binder type and addition amount. The film thickness indicates the thickness of each porous layer formed at the upper surface $8b$ side of the gas sensing layer 8. The first porous layer and/or second porous layer may be a metal supported layer and the properties of the first porous layer and the second porous layer may be changed by the metal type or the like. Further, the materials of the absorption layer 10 and the diffusion layer 9 are not limited, but if the diffusion layer 9 and the absorption layer 10 are formed of porous layers, they are each preferably formed from a metal oxide of at least one of $Al_2O_3$, $Cr_2O_3$, $Fe_2O_3$, $Ni_2O_3$, $ZrO_2$ and $SiO_2$ as main ingredient. With use of the metal oxide, the first porous layer is able to be formed as a layer having excellent absorption and the second porous layer is able to be formed as a layer having excellent diffusion appropriately and simply. By changing the materials of the first porous layer and the second porous layer, it is possible to change diffusion and absorption, but the diffusion layer 9 and the absorption layer 10 are preferably formed of the same material in order to improve adhesion between the diffusion layer 9 and the absorption layer 10. Accordingly, control of absorption and diffusion is preferably adjusted by other than the material of the porous layers. Particularly, by adjustment of average pore size, it is preferably possible to control the diffusion and absorption most simply and appropriately. Further, as illustrated in FIG. 1, by forming the film thickness of the absorption to be larger than the film thickness of the diffusion layer 9, it is possible to increase the absorption amount of measurement target gas G1 by the absorption layer 10.

In addition, the controller 11 as illustrated in FIG. 4 controls driving of the heater layer 4 and as illustrated in FIG. 7, the controller 11 is able to perform intermittent driving of the heater layer 4.

Thus, by driving the heater layer 4 intermittently, as explained in FIGS. 5A and 5B, after the measurement target gas G1 is absorbed and condensed, the measurement target gas G1 is able to be subjected to thermal desorption and diffusion in a short time. With this process, the concentration of trace gas can be increased, and thereby, it is possible to detect the trace gas highly sensitively. Further, the gas sensor 1 according to the present embodiment can be thinner by MEMS (Micro Electro Mechanical Systems), and in accordance with switch between on and off of driving of the heater layer 4, it is possible to expedite heat propagation to the gas detector 6 and heat shrinkage there from and thereby to switch between absorption and condensing of the measurement target gas G1 and thermal desorption and diffusion of the measurement target gas G1 instantaneously. Therefore, it is possible to provide a gas sensor that is excellent in response.

Thus, according to the present embodiment, while the heater layer 4 stops driving, the measurement target gas G1 is absorbed and condensed by the absorption layer 10. Then, when the heater layer 4 is driven, the measurement target gas G1 is thermally-desorbed from the absorption layer 10 and diffused from the diffusion layer 9 to the gas sensing layer 8, thereby making it possible to detect trace gas (for example, volatile organic compounds in the order of 0.01 to 1 ppm) more sensitively than the conventional case.

Further, in the present embodiment, as illustrated in FIGS. 5A and 5B, it is possible to give difference in absorption amount at the absorption layer 10 and diffusion in the diffusion layer 9 between the measurement target gas G1 and other gases G2 and G3. With this structure, it is possible to detect the trace measurement target gas G1 more sensitively.

For example, as illustrated in FIG. 5A, as for the gas G2, the absorption amount to the absorption layer 10 is than that of the measurement target gas G1, and the gas G3 is not absorbed to the absorption layer 10 (the thickness of each arrow shown in FIG. 5A indicates the absorption amount). For example, the gases G1, G2 and G3 are all volatile organic compounds and, as an example, the measurement target gas G1 is acetone, and the gases G2 and G3 are volatile organic compounds other than acetone (ethanol, methanol, toluene, xylene, ethyl acetate, formaldehyde, acetaldehyde, chloroform, para-dichlorobenzene or the like). Thus, the absorption amount of acetone is able to be greater than the absorption amounts of other volatile organic compounds by controlling the average pore size, average particle size, polarity, binder type, addition amount of the absorption layer 10 and so on.

Further, in the present embodiment, as illustrated in FIG. 5B, it is possible to control to cause difference in diffusion between the gases G1, G2 and G3 at the diffusion layer. Diffusion can be replaced with a diffusion speed and a diffusion amount inside the layer. Excellent diffusion means that the diffusion speed is higher and the diffusion amount is larger. In FIG. 5B, the diffusion of the measurement target gas G1 in the diffusion layer 9 is most excellent and diffusion of the gas G2 is second most excellent and the diffusion of gas G3 is the lowest. For example, the diffusion speed of the measurement target gas G1 is the fastest, the diffusion speed of the gas G2 is second fastest and the diffusion speed of the gas G3 is lowest. Therefore, it is possible to distinguish which to detect the measurement target gas G1 or the other gases G2 and G3 at the timing of obtaining the sensor output illustrated in FIG. 7 (time after the heater drive is turned on). Or, the measurement target gas G1 is not necessarily one kind, but may include two or more kinds of gases. For example, the gases G1 and G2 illustrated in FIGS. 5A and 5B are both set to be measurement target gases. As a sensor output illustrated in FIG. 7, it is possible to obtain sensor outputs of the gases G1 and G2 separately. Then, by making use of different timings of obtaining sensor outputs (reaching peak sensitivity) (timings of reacting with the gas sensing layer 8) depending on the gas types, it is possible to distinguish multiple measurement target gases from each other highly sensitively. For example, as for ethanol and acetone, the molecular mass of acetone is larger than that of ethanol. Therefore, the average pore size is adjusted in accordance with absorption and diffusion of acetone. At this time, as explained in the experiments given later, it is clear that ethanol and acetone do not have great difference in peak sensitivity, but have difference in timing of reaching the peak sensitivity. That is, since detection timing of acetone is later than that of ethanol, ethanol and acetone are able to be distinguished appropriately by combining such a time factor.

In the present embodiment, as illustrated in FIG. 5B, diffusion from the diffusion layer 9 to the gas sensing layer 8 varies depending on the kind of gas. For example, this difference in diffusion by the kind of gas is able to be controlled by controlling the heating temperature of the heater layer 4 and the layer structure of the diffusion layer 9. Particularly, when the gas detector 6 is heated by the heater layer 4, thermal desorption from the absorption layer 10 depends on the heating temperature. Accordingly, it is possible to expedite the thermal desorption from the absorption layer 10 effectively by controlling the heating temperature. In addition, by causing a diffusion difference depending on the kind of gas in the diffusion layer 9, it is possible to detect the measurement target gas 1 accurately by distinguishing it from other gases, thereby improving the detection sensitivity effectively.

Figure 2:
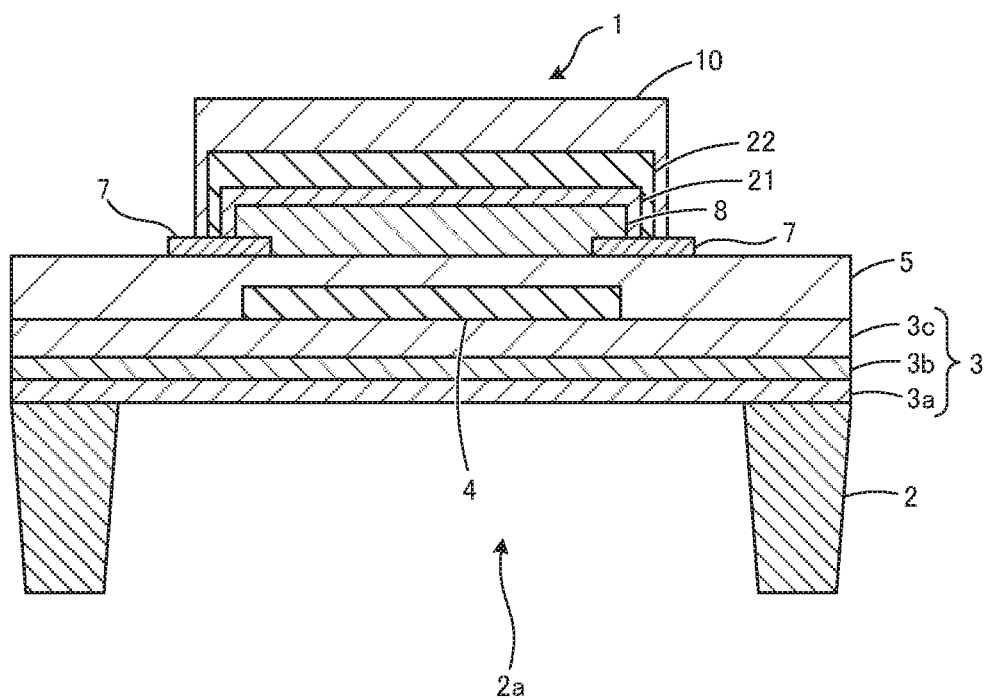
FIG. 2 is a longitudinal sectional view of a gas sensor according to a second embodiment.

FIG. 2 is a longitudinal sectional view of a gas sensor according to the second embodiment. In the embodiment shown in FIG. 2, the diffusion layer is a two-layer structure consisting of a first diffusion layer 21 and a second diffusion layer 22, unlike in FIG. 1. As illustrated in FIG. 2, the first diffusion layer 1 is formed on the surfaces of the gas sensing layer 8 and the second diffusion layer 22 is formed on the surfaces of the first diffusion layer 21. Then, the absorption layer 10 is formed over the surfaces of the second diffusion layer 22.

In FIG. 2, the absorption layer 10 is more excellent in absorption of the measurement target gas than the first diffusion layer 21 and the second diffusion layer 22. In addition, the second diffusion layer 22 has poor absorption of the measurement target gas as compared with the absorption layer 10 and the second diffusion layer 22, but the first diffusion layer 21 has more excellent diffusion of the measurement target gas as compared with the absorption layer 10 and the second diffusion layer 22. Illustrating the specific layer structure of the first diffusion layer 21, the second diffusion layer 22 and the absorption layer 10, the first diffusion layer 21 is formed of $Al_2O_3$ and has an average pore size of 14 nm, the second diffusion layer 22 is formed of $Al_2O_3$ and has an average pore size of 11 nm, and the absorption layer 10 is formed of $Al_2O_3$ and has an average pore size of 9.3 nm (see Examples given later). Thus, the first diffusion layer 21, the second diffusion layer 22 and the absorption layer 10 are made of the same material and are differentiated in average pore size such that the average pore size becomes smaller in the order of the first diffusion layer 21, the second diffusion layer 22 and the absorption layer 10, thereby making it possible to maintain good adhesion between the layers, to adjust diffusion easiness of the measurement target gas such that the first diffusion layer 21>the second diffusion layer 22>the absorption layer 10 and to adjust the absorption amount of the measurement target gas such that the absorption layer 10>the second diffusion layer 22>the first diffusion layer 21.

In FIG. 1, the diffusion layer 9 is a one-layer structure and in FIG. 2, the diffusion layer is a two-layer structure having the diffusion layers 21 and 22. However, the diffusion layer may be a three or more-layer structure. In such a case, diffusion is adjusted, for example by adjusting the average pore size so that diffusion becomes more excellent as the diffusion layer is closer to the gas sensing layer 8 and the layer (absorption layer 10) that is furthest from the gas sensing layer 8 exhibits more excellent absorption.

Figure 3:
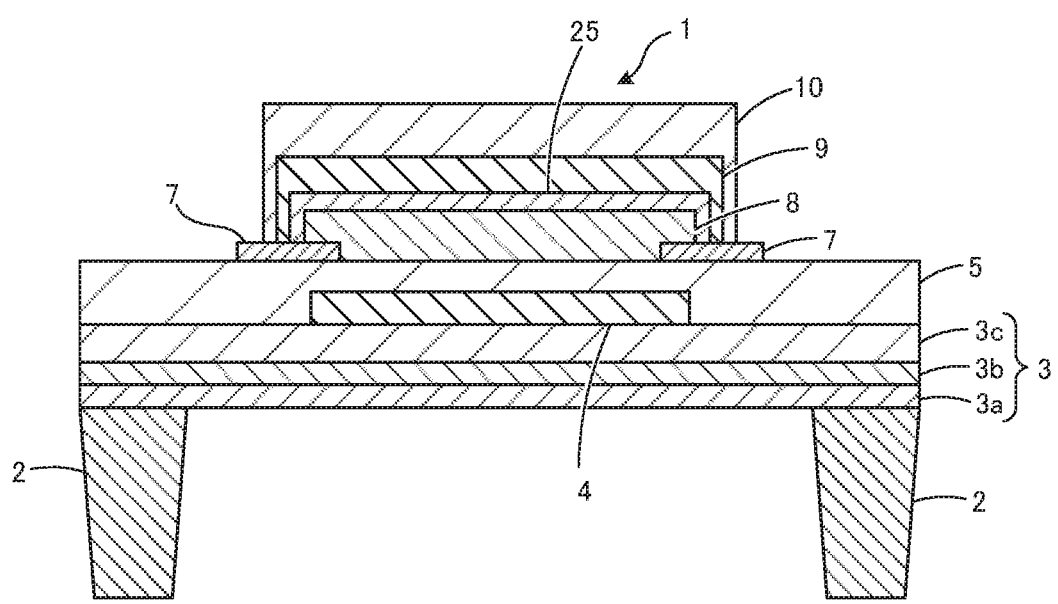
FIG. 3 is a longitudinal sectional view of a gas sensor according to a third embodiment.

FIG. 3 is a longitudinal sectional view of a gas sensor according to the third embodiment. In the embodiment illustrated in FIG. 3, an oxygen supply layer 25 is formed over the surfaces of the gas sensing layer 8. Then, the diffusion layer 9 is formed over the surfaces of the oxygen supply layer 25, and the absorption layer 10 is formed over the surfaces of the diffusion layer 9. That is, in the embodiment shown in FIG. 3, the multilayer structure is provided such that the oxygen supply layer 25 is provided between the gas sensing layer 8 and the diffusion layer 9.

The gas sensing layer 8 is, for example, an n-type semiconductor layer formed of $SnO_2$. The gas sensing layer 8 formed of $SnO_2$ is exposed to reducing gas, which causes reaction between oxygen adhered to the surface of the gas sensing layer 8 and the gas, resulting in reduction in concentration of oxygen at the surface. This results in increase in electrons (carriers) of the gas sensing layer 8 and reduction in resistance. On the other hand, assuming the gas sensing layer 8 is formed of $SnO_2$, when the gas sensing layer 8 is exposed to oxidation gas, the concentration of oxygen at the surface of the gas sensing layer 8 is increased, resulting in reduction in electrons (carriers) of the gas sensing layer 8 and increase in resistance. Since this reaction with gas is caused at the surface of the gas sensing layer 8, in order to improve the reaction sensitivity, there is preferably provided a layer for supplying oxygen to the surface of the gas sensing layer 8 (oxygen supply layer 25). For example, the gas sensing layer 8 is formed of a metal oxide layer containing dopant and the oxygen supply layer 25 is formed as a metal-supported catalyst layer is formed at least at the surface of the gas sensing layer 8. The types of gases are not limited specifically, but may include Pt, Pd, Ag, Au and so on. By forming the above-mentioned metal-supported catalyst layer on the surface of the gas sensing layer 8 as oxygen supply layer 25, it is possible to improve the reaction sensitivity appropriately and easily. Here, it is not necessary to clearly define the oxygen supply layer 25 in the gas sensing layer 8.

Figure 6A:
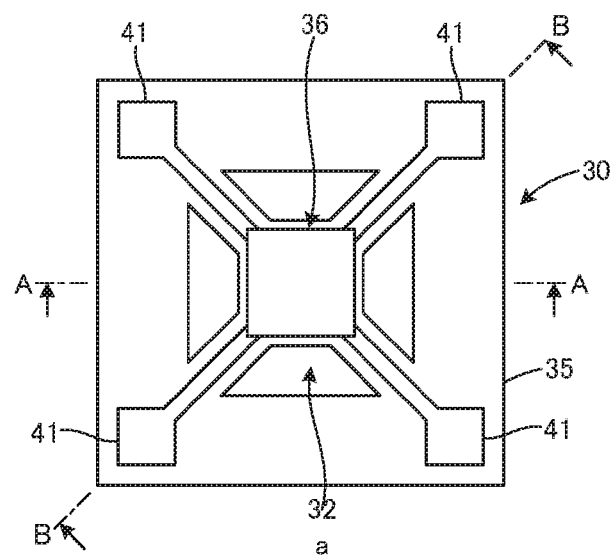
FIGS. 6A, 6B and 6C provide a plan view and longitudinal sectional views of a gas sensor according to another embodiment.
Figure 6B:
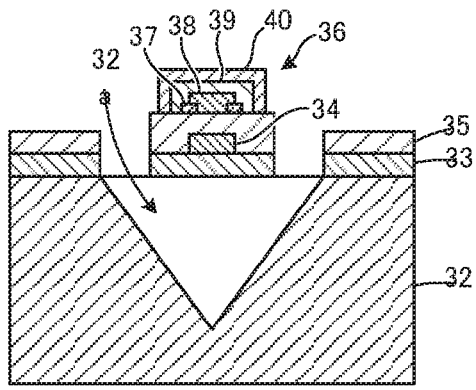
Figure 6C:
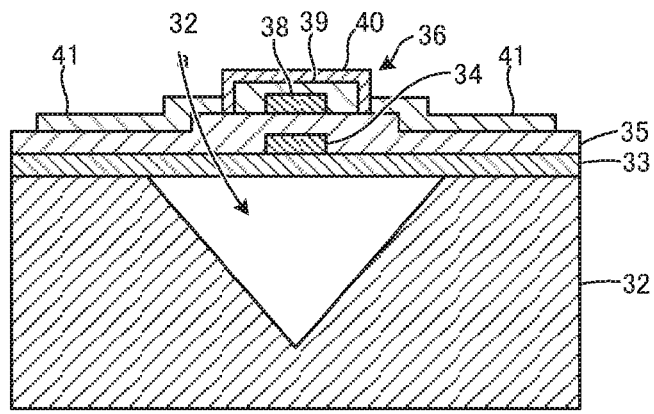

FIGS. 6A, 6B and 6C provide a plan view and two longitudinal sectional views of a gas sensor according to another embodiment. FIG. 6A is a plan view of the gas sensor, FIG. 6B is a longitudinal sectional view of the gas sensor taken along the line A-A and seen in the direction of the arrows, and FIG. 6C is a longitudinal sectional view of the gas sensor taken along the line B-B and seen in the direction of the arrows. The gas sensor in FIGS. 6A, 6B and 6C is a gas sensor 30 of cross-linked structure. Like the diaphragm shown in FIGS. 1 to 3, this cross-linked structure becomes a highly-insulating and low-heat capacity structure and can be used as a gas sensor for detecting trace gas. As illustrated in each view of FIGS. 6A, 6B and 6C, the gas sensor 30 has a silicon substrate 32, a heat insulating layer 33, a heater layer 34, an electric insulating layer 35 and a gas detector 36. As illustrated in FIGS. 6B and 6C, the silicon substrate 32 has a closed-end recess part (cavity) 32a formed therein, and as illustrated in FIG. 6A, the cross-linking structure is formed on the recess part 32a. The heat insulating layer 33 is equivalent to the heat insulating layer 3 illustrated in FIG. 1, the heater layer 34 is equivalent to the heater layer 4 illustrated in FIG. 1, the electric insulating layer 35 is equivalent to the electric insulating layer 5 illustrated in FIG. 1, and the gas detector 36 is equivalent to the gas detector 6 illustrated in FIG. 1. As illustrated in FIG. 6B, the gas detector 36 is configured to include a gas sensing layer 38, sensing layer electrodes 37, a diffusion layer 39 and an absorption layer 40. The gas sensing layer 38 is equivalent to the gas sensing layer 8 illustrated in FIG. 1, sensing layer electrodes 37 are equivalent to the sensing layer electrodes 7 illustrated in FIG. 1, the diffusion layer 39 is equivalent to the diffusion layer 9 illustrated in FIG. 1, and the absorption layer 40 is equivalent to the absorption layer 10 illustrated in FIG. 1. As illustrated in FIGS. 6A and 6C, on the electric insulating layer 35, a wiring conductive layer 41 is formed that is electrically connected to the sensing layer electrodes 37 and the heater layer 34.

The gas detection principle in the embodiment shown in FIGS. 6A, 6B and 6C is the same as that shown in FIGS. 5A and 5B. Also in the embodiment shown in FIGS. 6A, 6B and 6C, the diffusion layer may be a two-layer structure like in FIG. 2 and the oxygen supply layer may be placed over the surfaces of the gas sensing layer 38, Like in FIG. 3.

Next description is made about a method of manufacturing a gas sensor illustrated in FIG. 1. First, a silicon substrate 2 is prepared with thermally-oxidized films formed on both surfaces, and a heat insulating layer 3 is deposited on the surface of the silicon substrate 2 by the CVD method. The structure of the heat insulating layer 3 may have a three-layer structure as illustrated in FIG. 1 or any other layer structure. Then, a heater layer 4 is formed on the heat insulating layer 3. As is not shown in FIG. 1, at this time, a wiring layer is also formed to be connected to the heater layer 4. The heater layer 4 may be deposited by sputtering method or the like. Next, an electric insulating layer 5 formed of $SiO_2$ and so on is formed on the surfaces of the heater layer 4 by the sputtering method or the like.

Then, sensing layer electrodes 7 formed of Pt or the like and a gas sensing layer 8 formed of $SnO_2$ or the like are deposited on the electric insulating layer 5 by the sputtering method or the like. When forming the sensing layer electrodes 7, a bonding layer formed of Ta, Ti or the like (not shown) is formed in advance and the sensing layer electrodes 7 are formed on the bonding layer. With this process, it is possible to improve adhesion between the sensing layer electrodes 7 and the electric insulating layer 5.

Next, a diffusion layer 9 is formed on the surfaces of the gas sensing layer 8. The diffusion layer 9 is formed by preparing a paste such that porous materials of $Al_2O_3$ and binder resin are mixed in solvent applying the paste to entire surfaces of the gas sensing layer 8 by the screen printing, dispensing, inkjet or any other method, drying it at temperatures of 100° C. to 200° C. and then calcining the resultant (for example, 500° C. or more). The binder and viscous agent (resin) may be thermoplastic resin such as polyethylene resin or ethyl cellulose.

In the following step, an absorption layer 10 is formed over the surfaces of the diffusion layer 9. The absorption layer 10 is formed by preparing a paste such that porous materials of $Al_2O_3$ (which are, however, different from the porous materials used in the diffusion layer 9) and binder resin are mixed in solvent applying the paste to entire surfaces of the diffusion layer 9 by the screen printing, dispensing, inkjet or any other method and drying the resultant, for example, at temperatures of 100° C. to 200° C. For example, the porous materials used in the absorption layer 10 have a smaller average pore size than the porous materials used in the diffusion layer 9. With this feature, it is possible to make the absorption layer 10 have more excellent gas-absorption than the diffusion layer 9, and also possible to make the diffusion layer 9 have more excellent diffusion than the absorption layer 10. Further, by forming the absorption layer 10 to be a thicker than the diffusion layer 9, it is possible to increase the gas absorption amount of the absorption layer 10 effectively.

As illustrated in FIG. 2, when the diffusion layer is a multilayer structure consisting of the first diffusion layer 21 and the second diffusion layer 22, in order to increase diffusion of the first diffusion layer 21 more than diffusion of the second diffusion layer 22, for example, the average pore size of porous materials used in the first diffusion layer 21 is made larger than the average pore size of porous materials used in the second diffusion layer 22. In addition, in order to increase absorption of the absorption layer 10 more than absorption of the first diffusion layer 21 and absorption of the second diffusion layer 22, for example, the average pore size of porous materials used in the absorption layer 10 is made smaller than the average pore size of porous materials used in the first diffusion layer 21 and the second diffusion layer 22.

As illustrated in FIG. 3, when the oxygen supply layer 25 is formed on the surfaces of the gas sensing layer 8, metal supporting processing is performed on the surfaces of the gas sensing layer 8 to form a metal supported layer. With this process, the surfaces of the gas sensing layer 8 are able to be a layer having excellent oxygen supply property.

The step of forming a through hole 2a in the silicon substrate 2 is not limited as far as it is performed after forming the heat insulating layer 3. However, if the through hole 2a is formed at least after the electric insulating layer 5 is formed, it is possible to keep high rigidity of the multilayer structure over the through hole 2a when the through hole 2a is formed, thereby allowing easy and appropriate forming of the gas detector 6. The through hole 2a is formed by dry etching. With this forming, fine shape control is enabled.

The gas sensor 30 illustrated in FIGS. 6A, 6B and 6C is manufactured by a manufacturing method conforming to the above-described method for manufacturing a gas sensor. However, a recess part (cavity) 32a is formed by wet etching. In wet etching, the fine shape control is more difficult than that in dry etching, but it is possible to provide simple manufacturing without any expensive equipment.

The gas sensor according to the present embodiment is applicable, for example, to a breath sensor, but is not limited to this and may be used for biomedical, health-care, living space, auto exhausts, automobile and quality management purposes, without limiting application purposes specifically. Besides, there is no limitation on the kinds of measurement target gases. The measurement target gas includes, in addition to the volatile organic compounds (VOC) mentioned above, air pollution gas, poisonous gas rom factories and so on. The gas sensor according to the present embodiment is able to be used for detecting trace volatile organic compounds preferably.

EXAMPLES

Next description is made about examples that have been conducted to confirm the effect of the present invention. These examples, however, are not intended to limit the present invention.

Experiment on Different Average Pore Sizes

In the experiment, $Al_2O_3$ (average pore size: 9.3 nm) is used as sample A, $Al_2O_3$ (average pore size: 11 nm) is used as sample B and $Al_2O_3$ (average pore size: 14 nm) is used as sample C.

Figure 8:
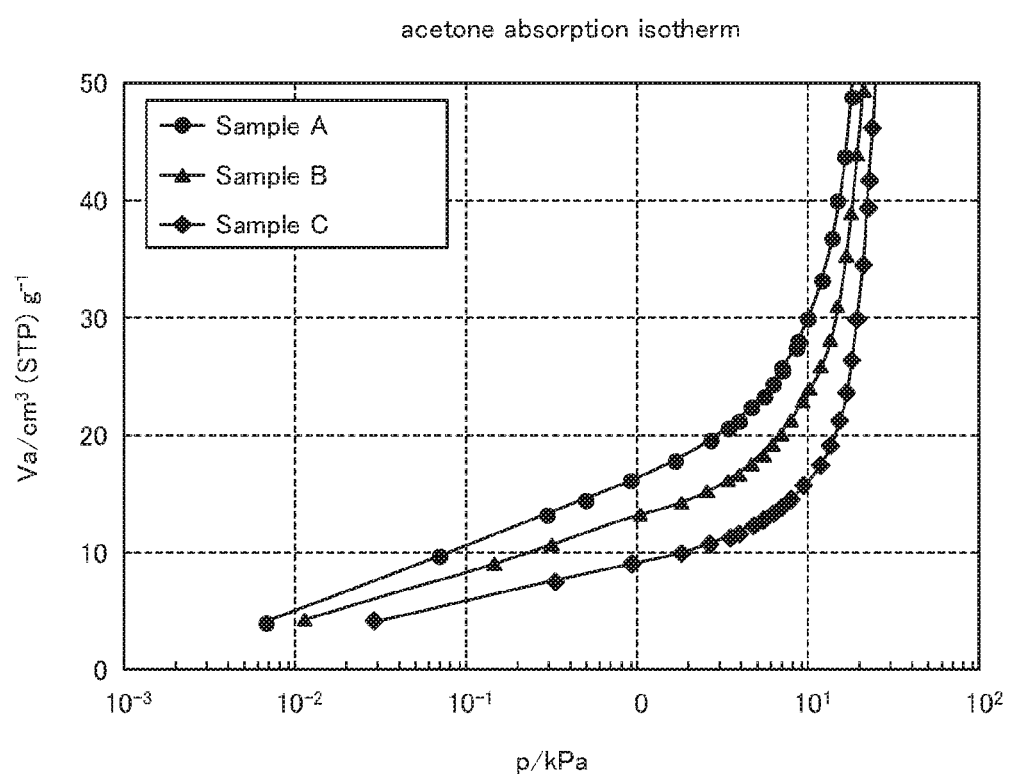
FIG. 8 is a graph showing acetone absorption isotherm of a porous material formed of $Al_2O_3$ of different average pore sizes.

Then, acetone is used as an absorption gas for each porous material and the acetone absorption isotherm is achieved at 25° C. Measurement of the acetone absorption isotherm is performed using a BELSORP-max by Microtrac BEL Corp. Its experimental result is shown in FIG. 8. As illustrated in FIG. 8, at constant pressure, the sample A of the smallest average pore size exhibits greater absorption amount than the samples B and C. The following table 1 shows absorption amounts of each sample at the pressures of 0.01 kPa and 0.1 kPa.

TABLE 1

| | SAMPLE | | |
|---|---|---|---|
| | A | B | C |
| PORE SIZE (nm) | 9.3 | 11 | 14 |
| ABSORPTION AMOUNT 0.01 kPa ($cm^3(STP)g^{-1}$) | 4.40 | 4.24 | 3.94 |
| 0.1 kPa | 10.28 | 7.50 | 4.97 |

At the pressure of 0.1 kPa, the absorption amount of sample A is 1.4 times greater than the absorption amount of sample B and is 2 times greater than the absorption amount of sample C.

Further, the average pore size of the porous material of sample B is greater than the average pore size of the porous material of sample A, and sample B is more excellent in diffusion than sample A. The average pore size of the porous material of sample C is greater than the average pore sizes of the porous materials of samples A and B, and sample C is more excellent in gas diffusion than samples A and B.

From this experimental result, it has been proved that preferably, the porous material of sample A is used as the absorption layer, and when the diffusion layer is a single-layer structure, either of the porous material of sample B and the porous material of sample C and when the diffusion layer is a two-layer structure, the porous material of sample C is used as the first diffusion layer that is closest to the gas sensing layer, and the porous material of sample B is used as the second diffusion layer that is placed between the first diffusion layer and the absorption layer.

Experiment on Difference in Detection Time Depending on Gas Type

Then, experiment has been conducted to study the relationship between the detection time and gas sensitivity for ethanol and acetone. The diffusion layer 9 is formed of sample C and the absorption layer 10 is formed of sample A. In addition, the driving condition of the heater layer 4 is unified such that the voltage is 1.44 V and the cycle is 20 s. Its experimental result is shown in FIG. 9.

Figure 9A:
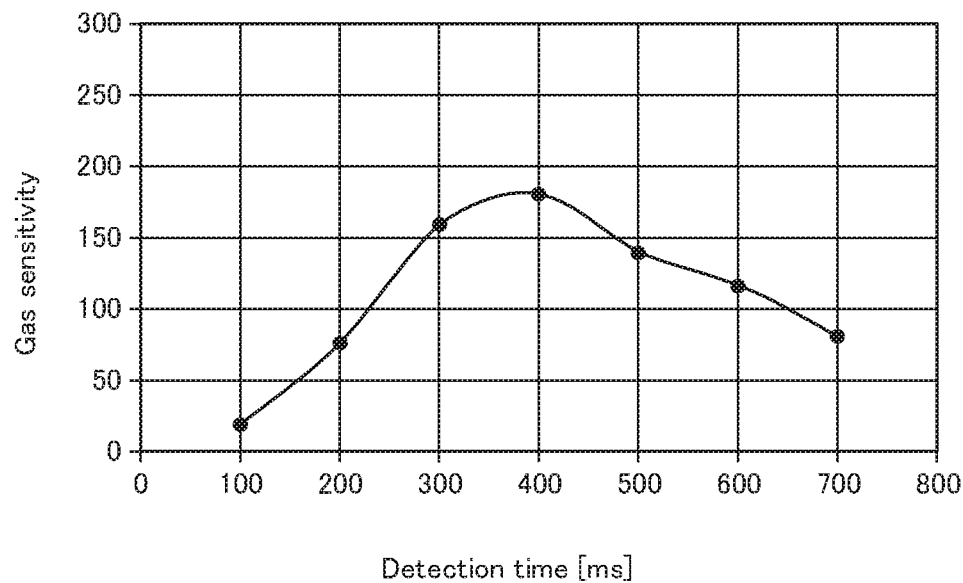
FIG. 9A is a graph illustrating the relationship between ethanol detection time and gas sensitivity.
Figure 9B:
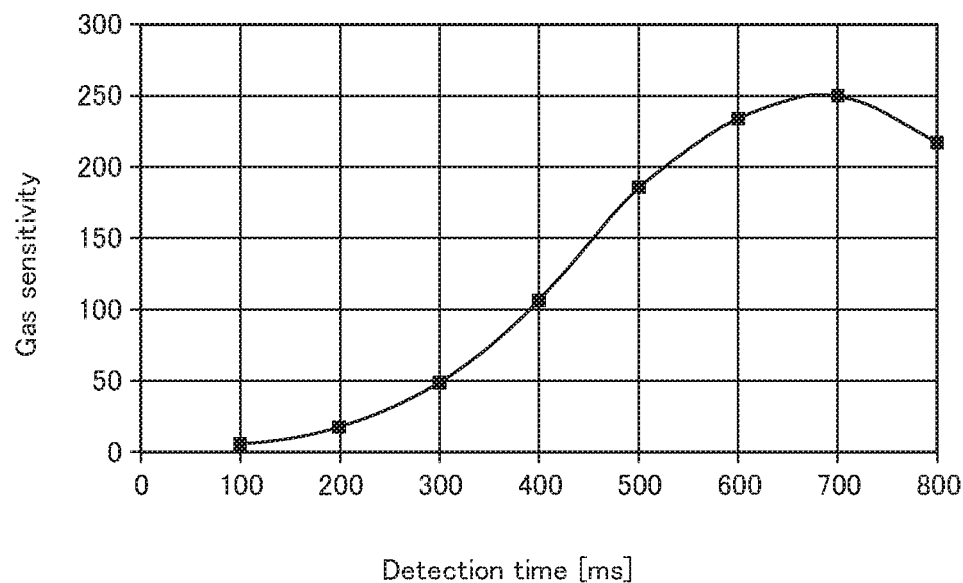
FIG. 9B is a graph showing the relationship between acetone detection time and gas sensitivity.

As illustrated in FIG. 9A, in the case of ethanol, when the detection time is 400 ms, the gas sensitivity reaches a peak value and in the case of acetone, when the detection time is 700 ms, the gas sensitivity reaches a peak value.

In this way, as there is difference in timing (detection time) of reaching the peak sensitivity depending on the types of gases, it has been found that the gas types are able to be distinguished based on difference in detection timing.

According to the gas sensor of the present invention, it is possible to detect trace volatile organic compounds in the order of 0.01 to 1 ppm highly sensitively, and the gas sensor of the present invention is an MEMS-manufactured, battery-operated semiconductor gas sensor and is capable of realizing miniaturization and low power consumption. Therefore, the gas sensor is able to be installed on various places and sites, and is also able to be used as a breath sensor, an exhaust gas detection sensor, an air pollution detection sensor in living spaces, factories or the like.

The present invention is not limited to the above-described embodiments and may be embodied in various modified forms. In the above-described embodiments, the size and shape are not limited to those illustrated in accompanying drawings, and may be modified appropriately as far as the effects of the present invention can be exerted. Other modifications may be also made appropriately without departing from the scope of the object of the present invention.

What is claimed is:

1. A gas sensor for detecting a target gas to be measured when desorbed, comprising:
   a heater layer; and
   a gas detector that is heated by the heater layer for desorption of the target gas in use, and that is comprised of:
      a gas sensing layer provided proximate to the heater layer and comprised of a material effective for sensing the target gas when desorbed;
      at least one diffusion layer positioned to cover the gas sensing layer and comprised of a porous material which has a pore size effective for diffusion of the target gas there through; and
      an absorption layer positioned to cover the at least one diffusion layer and comprised of a porous material which has a pore size effective for absorption of the target gas,
   wherein the absorption layer has greater absorption of the target gas than the at least one diffusion layer and the at least one diffusion layer has greater diffusion of the target gas than the absorption layer due to a difference there between of at least one of average pore size, average particle size, specific surface area, polarity, film thickness, supported metal, and constituent porous material.

2. The gas sensor according to claim 1, wherein the porous material of the absorption layer has an average pore size that is smaller than that of the porous material of the at least one diffusion layer.

3. The gas sensor according to claim 2, wherein the at least one diffusion layer comprises two or more layers, and one layer of the two or more layers that is closer to the gas sensing layer has a greater average pore size.

4. The gas sensor according to claim 1, further comprising a controller that controls is electrically connected to the heater layer and to the gas sensing layer, that is programmed to control the heater layer to intermittently drive the heater layer in use, and that obtains a sensor output from the gas sensing layer,
   wherein the controller controls the heater layer to intermittently drive the heater layer, and the target gas supplied from the diffusion layer is detected when a reaction occurs between the target gas and the gas sensing layer, and
   wherein, when the heater layer is at ambient temperature, the target gas is absorbed by the absorption layer and, when the heater layer is driven by the controller and is heated, the target gas is thermally desorbed from the absorption layer and diffuses into the diffusion layer toward the gas sensing layer.

5. The gas sensor according to claim 1, wherein the absorption layer and the at least one diffusion layer are each composed of at least one metal oxide selected from the group consisting of $Al_2O_3$, $Cr_2O_3$, $Fe_2O_3$, $Ni_2O_3$, $ZrO_2$ and $SiO_2$, as a main ingredient.

6. The gas sensor according to claim 1, further comprising an oxygen supply layer formed at least on the surface of the gas sensing layer between the gas sensing layer and the at least one diffusion layer.

7. The gas sensor according to claim 1, wherein the gas sensing layer is formed of a metal oxide layer containing a dopant.

8. The gas sensor according to claim 1, further comprising:
a substrate;
a heat insulating layer formed on a surface of the substrate;
the heater layer formed on a surface of the heat insulating layer;
an electric insulating layer formed on a surface of the heater layer;
the gas sensing layer formed on a surface of the electric insulating layer;
an electrode layer connected to the gas sensing layer;
the diffusion layer formed on the surface of the gas sensing layer; and
the absorption layer formed on the surface of the diffusion layer,
wherein the substrate has defined therein a through hole formed to communicate with the heat insulating layer or has a closed-end cavity formed between the substrate and the heat insulating layer.

9. A gas sensor for detecting a target gas to be measured when desorbed, comprising:
a heater layer; and
a gas detector that is heated by the heater layer for desorption of the target gas in use, and that is comprised of:
a gas sensing layer provided proximate to the heater layer and comprised of a metal oxide layer containing a dopant that is effective for sensing the target gas;
at least one diffusion layer positioned to cover the gas sensing layer and comprised of a porous material which is effective for diffusion of the target gas there through; and
an absorption layer positioned to cover the at least one diffusion layer and comprised of a porous material which has a pore size effective for absorption of the target gas; and
a controller that is electrically connected to the heater layer and to the gas sensing layer, that is programmed to control the heater layer to intermittently drive the heater layer in use, and that obtains a sensor output from the gas sensing layer,
wherein the absorption layer has greater absorption of the target gas than the diffusion layer and the diffusion layer has greater diffusion of the measurement target gas than the absorption layer due to a difference there between of at least one of average pore size, average particle size, specific surface area, polarity, film thickness, supported metal, and constituent porous material; and
wherein the absorption layer and the at least one diffusion layer are each composed of at least one metal oxide selected from the group consisting of $Al_2O_3$, $Cr_2O_3$, $Fe_2O_3$, $Ni_2O_3$, $ZrO_2$ and $SiO_2$, as a main ingredient.

10. The gas sensor according to claim 9, wherein the porous material of the absorption layer has an average pore size that is smaller than that of the porous material of the at least one diffusion layer.

11. The gas sensor according to claim 10, wherein the at least one diffusion layer comprises two or more layers, and one layer of the two or more layers that is closer to the gas sensing layer has a greater average pore size.

12. A gas sensor for detecting a target gas to be measured when desorbed, comprising:
a substrate;
a heat insulating layer formed on a surface of the substrate;
a heater layer formed on a surface of the heat insulating layer;
an electric insulating layer formed on a surface of the heater layer;
a gas detector that is intermittently heated by the heater layer for desorption of the target gas in use, and that is comprised of:
a gas sensing layer formed on a surface of the electric insulating layer proximate to the heater layer and comprised of a material effective for sensing the target gas when desorbed;
an electrode layer connected to the gas sensing layer;
at least one diffusion layer formed on a surface of the gas sensing layer to cover the gas sensing layer and comprised of a porous material which has a pore size effective for diffusion of the target gas there through; and
an absorption layer formed on a surface of the diffusion layer to cover the surface of the at least one diffusion layer and comprised of a porous material which has a pore size effective for absorption of the target gas,
wherein the substrate has defined therein a through hole formed to communicate with the heat insulating layer or has a closed-end cavity formed between the substrate and the heat insulating layer, and
wherein the absorption layer has greater absorption of the target gas than the diffusion layer and the at least one diffusion layer has greater diffusion of the target gas than the absorption layer due to a difference there between of at least one of average pore size, average particle size, specific surface area, polarity, film thickness, supported metal, and constituent porous material.

13. The gas sensor according to claim 12, wherein the porous material of the absorption layer has an average pore size that is smaller than that of the porous material of the at least one diffusion layer.

14. The gas sensor according to claim 13, wherein the at least one diffusion layer comprises two or more layers, and one layer of the two or more layers that is closer to the gas sensing layer has a greater average pore size.

15. The gas sensor according to claim 12, further comprising a controller that is electrically connected to the heater layer and to the gas sensing layer, that is programmed to control the heater layer to intermittently drive the heater layer in use, and that obtains a sensor output from the gas sensing layer,
wherein the controller controls the heater layer to intermittently drive the heater layer, and the target gas supplied from the diffusion layer is detected when a reaction occurs between the measurement target gas and the gas sensing layer, and
wherein, when the heater layer is at ambient temperature, the target gas is absorbed by the absorption layer and, when the heater layer is driven by the controller and is heated, the target gas is thermally desorbed from the absorption layer and diffuses into the diffusion layer toward the gas sensing layer.

16. The gas sensor according to claim 12, wherein the absorption layer and the at least one diffusion layer are each composed of at least one metal oxide selected from the group consisting of $Al_2O_3$, $Cr_2O_3$, $Fe_2O_3$, $Ni_2O_3$, $ZrO_2$ and $SiO_2$, as a main ingredient.

17. The gas sensor according to claim 12, further comprising an oxygen supply layer formed at least on the surface of the gas sensing layer between the gas sensing layer and the at least one diffusion layer.

18. The gas sensor according to claim 12, wherein the gas sensing layer is formed of a metal oxide layer containing a dopant.

* * * * *